United States Patent [19]

Campbell et al.

[11] Patent Number: 4,728,654
[45] Date of Patent: Mar. 1, 1988

[54] QUINOLONE INOTROPIC AGENTS

[75] Inventors: Simon F. Campbell, Deal; David A. Roberts, Sandwich, both of England

[73] Assignee: Pfizer Inc., New York, N.Y.

[21] Appl. No.: 822,575

[22] Filed: Jan. 27, 1986

[30] Foreign Application Priority Data

Jan. 30, 1985 [GB] United Kingdom ................ 8502267

[51] Int. Cl.$^4$ .................... A61K 31/47; C07D 215/06; C07D 401/10; C07D 401/12
[52] U.S. Cl. .................................... 514/312; 546/157; 546/180; 546/2; 564/202
[58] Field of Search ................ 514/312; 546/157, 158, 546/173, 275, 298

[56] References Cited

U.S. PATENT DOCUMENTS

| 3,287,459 | 11/1966 | Zimmer et al. | 546/157 |
|---|---|---|---|
| 3,668,207 | 6/1972 | Carney | 544/128 |
| 3,810,896 | 5/1974 | Witte et al. | 544/376 |
| 3,810,898 | 5/1974 | Witte et al. | 544/376 |
| 4,004,012 | 1/1977 | Lesher et al. | 514/334 |
| 4,234,585 | 11/1980 | Winter et al. | 544/363 |
| 4,503,061 | 3/1985 | Bristol et al. | 546/128 |

FOREIGN PATENT DOCUMENTS

| 148623 | 7/1985 | European Pat. Off. | 546/157 |
|---|---|---|---|
| 166533 | 1/1986 | European Pat. Off. | 546/157 |

OTHER PUBLICATIONS

Tomisawa et al., Yakugaku Zasshi, 87, pp. 554–557, (1967).
Yoshitomi Pharm. Derwent Abstract #31558b/17 for Be. patent –871310, 4/17/79.
Bormann, Chem. Abstracts, 96: 35107z (1982).
Juraszyk et al., Chem. Abstracts, 104:224890u (1986).
Sircar, Chem. Abstracts, 105:172313g (1986).
Herbert O. House, "Modern Synthetic Reactions", W. A. Benjamin, Inc. (1965), p. 9.
Muller, Chem. Abstracts, 101:7049k (1984).
E. Ziegler et al., "Synthesen von Heterocyclen," *Monatsh. Chem.*, vol. 98(2), pp. 324–328 (1967).
Chemical Abstracts, vol. 67, 54018 p(1967).
H. Balli et al., "Synthese von 1-Äthyl-2-azido-6-X--chinolinium-fluoroboraten," *Helvetica Chimica Acta*, vol. 53, Fasc. &(1970)–Nr. 223.
E. Schröder et al., "Nichsteroidale Entzudungshemmer 4,(1) Substituerte Azanaphthyl–essigsauren met anti-14 phlogistischer Wirkung," *Eur. J. Med. Chim.--Chemica–Therapeutica*, Nov.–Dec., 1979–14, No. 6, pp. 499–506.
T. Manimaran, et al., "Synthesis of Coumarins, Thiacoumarins & Carbostyrils," *Indian Journal of Chemistry*, vol. 18B, Oct. 1979, pp. 324–330.

*Primary Examiner*—Donald G. Daus
*Assistant Examiner*—E. Bernhardt
*Attorney, Agent, or Firm*—Peter C. Richardson; Lawrence C. Akers

[57] ABSTRACT

A series of novel phenyl-substituted 2-(1H)-quinolone compounds have been prepared, including the 3,4-dihydro derivatives thereof, wherein the phenyl ring moiety is a mono-or di-substituted phenyl group attached to the 5-, 6-, 7- or 8-positions of the quinolone ring. These particular compounds are useful in therapy as highly potent inotropic agents and therefore, are of value in the treatment of various cardiac conditions. Preferred member compounds include 8-methyl-6-[4-methylsulphinylphenyl]-2-(1H)-quinolone, 8-methyl-6-[4-hydroxyphenyl]-2-(1H)-quinolone and 8-methyl-6-[4-carbamoylphenyl]-2-(1H)-quinolone, respectively. Methods for preparing these compounds from known starting materials are provided.

8 Claims, No Drawings

QUINOLONE INOTROPIC AGENTS

BACKGROUND OF THE INVENTION

This invention relates to substituted quinolone cardiac stimulants which in general selectively increase the force of myocardial contraction without producing significant increases in the heart rate. The compounds are useful in the curative or prophylactic treatment of cardiac conditions, in particular in the treatment of heart failure.

SUMMARY OF THE INVENTION

Thus according to the present invention there are provided compounds having the general formula:

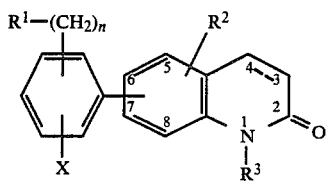

where n is 0, 1 or 2;

$R^1$ is selected from —$NR^4R^5$, —$NR^4CO(C_1-C_4$ alkyl), —$NR^4CONR^4R^5$, —$NR^4COOR^5$, —$S(O)_m(C_1-C_4$ alkyl), —$SO_2NR^4R^5$, —$NR^4SO_2R^5$, —$OCONR^4R^5$, —$OCO(C_1-C_4$ alkyl), —$OR^5$, —$OCH_2.Het$, —$COOR^4$, —$CONR^4R^5$ and Het';

$R^4$ is H or $C_1-C_4$ alkyl and $R^5$ is H, $C_1-C_4$ alkyl or —$CH_2CH_2N(C_1-C_2$ alkyl)$_2$, or $R^4$ and $R^5$ taken together with the nitrogen atom to which they are attached form a saturated 5- or 6-membered heterocyclic group optionally containing a further heteroatom or group selected from O, S and N—$R^6$ where $R^6$ is H or $C_1-C_4$ alkyl;

m is 0, 1 or 2;

Het is a 5- or 6-membered nitrogen-containing aromatic heterocyclic group attached by a carbon atom to the adjacent —$CH_2$— group;

Het' is a 5- or 6-membered nitrogen-containing heterocyclic group;

$R^2$, which is attached to the 3-, 4-, 5-, 6-, 7- or 8-position, is H, $C_1-C_4$ alkyl, $C_1-C_4$ alkoxy, hydroxy, cyano, halo, $CF_3$ or —$NR^4R^5$ where $R^4$ and $R^5$ are as defined above;

$R^3$ is H or $C_1-C_4$ alkyl;

X is H, $C_1-C_4$ alkyl, $C_1-C_4$ alkoxy, hydroxy, halo or $CF_3$;

and the dotted line between the 3- and 4-positions represents an optional bond;

and the pharmaceutically acceptable salts of the compounds of the formula (I).

When $R^4$ and $R^5$ together with the nitrogen atom to which they are attached form a saturated 5- or 6-membered heterocyclic group, typical examples of this group are 1-pyrrolidinyl, piperidino, morpholino and 4-methylpiperazin-1-yl.

Examples of Het include pyridyl, pyrazinyl, pyrmidinyl, pyridazinyl, imidazolyl, pyrazolyl, oxazolyl, isoxazolyl, thiazolyl, isothiazolyl, triazolyl and tetrazolyl, all these being linked by a ring carbon atom to the adjacent —$CH_2$— group, and all being optionally substituted by 1 or 2 substituents each independently selected from, e.g., $C_1-C_4$ alkyl, $C_1-C_4$ alkoxy, $C_1-C_4$ alkylthio, cyano, $CF_3$, halo, hydroxymethyl, ($C_1-C_4$ alkoxy)carbonyl, —$NR^4R^5$ and —$CONR^4R^5$ where $R^4$ and $R^5$ are as defined for formula (I).

Examples of Het' include the groups specified for Het above although these can be attached to the adjacent group by a carbon or nitrogen atom of the heterocyclic ring. In addition, Het' can be a saturated nitrogen-containing heterocyclic group such as piperidino, 1-pyrrolidinyl, morpholino, piperazinyl or N-methylpiperazinyl.

"Halo" means F, Cl, Br and I. $C_3$ and $C_4$ alkyl and alkoxy groups can be straight or branched chain. The preferred alkyl and alkoxy groups are methyl and methoxy.

Although the compounds of the formula (I) are written as 2-(1H)-quinolones, it should be realised that the following tautomerism can occur when $R^3$ is H:

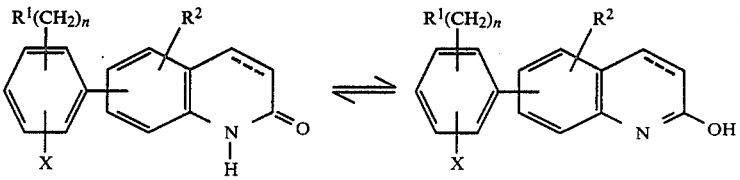

However, as the keto-form is considered the more stable tautomer, the end products herein will be named and illustrated as quinolones although those skilled in the art will realise that both tautomers may be present or that any particular compound so named may exist predominantly as the hydroxy tautomer and the following disclosure is to be interpreted to incorporate all tautomeric forms.

Preferably, there is a double bond in the 3,4-position.

The phenyl ring is preferably attached to the 6-position of the quinolone. "n" is preferably zero. X is preferably H. $R^2$ is preferably H or $CH_3$. When $R^2$ is $CH_3$ it is preferably in the 8-position of the quinolone. $R^3$ is preferably H. The group $R^1(CH_2)_n$— is preferably in the ortho or para position in the benzene ring, and is most preferably para.

Preferably n is 0 and $R^1$ is —$S(O)_mC_1-C_4$ alkyl where m is 0, 1 or 2, —$SO_2NH_2$, —$SO_2NH(C_1-C_4$ alkyl), —$SO_2N(C_1-C_4$ alkyl)$_2$, —$NHSO_2(C_1-C_4$ alkyl), —$NH_2$, —O.($C_1-C_4$ alkyl), —OH, —COOH, —$COO(C_1-C_4$ alkyl), —$CONH_2$, —$CON(C_1-C_4$ alkyl)$_2$, imidazol-1-yl, —$OCH_2$(pyridyl), —$OCH_2CH_2N(C_1$ or $C_2$ alkyl)$_2$, —$CON(C_1-C_4$ alkyl)$CH_2CH_2N(C_1$ or $C_2$ alkyl)$_2$ or —$OCONH(C_1-C_4$ alkyl).

More preferably, n is 0 and $R^1$ is —$S(O)_mCH_3$ where m is 0, 1 or 2, —$SO_2NH_2$, —$SO_2NHCH_3$, —$NHSO_2CH_3$, —$SO_2N(CH_3)_2$, —$NH_2$, —$OCH_3$, —OH, —COOH, —$COOCH_3$, —$CONH_2$, —$CON(CH_3)_2$, imidazol-1-yl, —$OCH_2$(4-pyridyl), —$OCH_2CH_2N(CH_3)_2$, —$CON(CH_3)CH_2CH_2N(CH_3)_2$ or —$OCONH$(n-propyl).

In the present application, the most preferred individual compounds of the formula (I) have the formula:

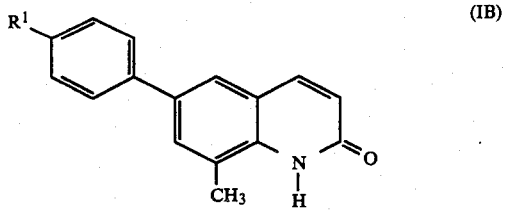

where $R^1$ is as defined for formula (I) and is preferably —SOCH₃, —OH or —CONH₂.

The most preferred individual compounds have the formula (IB) where $R^1$ is —CONH₂ or —SOCH₃.

The pharmaceutically acceptable salts of the compounds of the formulae (I) are either acid addition salts formed from acids which form non-toxic acid addition salts containing pharmaceutically acceptable anions, such as the hydrochloride, hydrobromide, hydroiodide, sulphate or bisulphate, phosphate or hydrogen phosphate, acetate, maleate, fumarate, lactate, tartrate, citrate, gluconate, methanesulphonate and p-toluenesulphonate salts, or are alkali metal or alkaline earth metal salts, particularly the sodium and potassium salts. When $R^1$ is, for example, carboxy and $R^3$ is H then salt formation is of course possible at two sites in the molecule, e.g.:

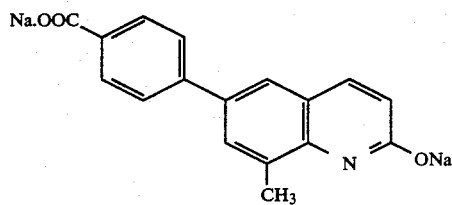

The cardiac stimulant activity of the compounds of the formula (I) is shown by their effectiveness in one or more of the following tests: (a) increasing the force of contraction in the "Starling" dog heart—lung preparation measured via a left ventricular catheter; (b) increasing myocardial contractility (left ventricular dp/dt max.) in the anaesthetised dog measured via a left ventricular catheter; (c) increasing myocardial contractility in the conscious dog with an implanted left ventricular transducer (dp/dt max.) or an exteriorised carotid artery loop (systolic time intervals).

In test (a), the positive inotropic effect of the test compound following bolus administration is measured in the "Starling" dog heart-lung preparation. The selectivity for increase in force versus frequency of contraction of the test compound is obtained.

In test (b), the positive inotropic action of the test compound following intravenous administration is measured in the anaesthetised dog. The magnitude and duration of this action, and the selectivity for increase in force versus frequency of contraction of the test compound are obtained, as are the peripheral effects, e.g. the effect on blood pressure.

In test (c) the positive inotropic action of the test compound following intravenous or oral administration to a conscious dog with an implanted left ventricular transducer (dp/dt max.) or an exteriorised carotid artery loop (systolic time intervals) is measured. The magnitude of the inotropic action, the selectivity for increase in force versus frequency of contraction, and the duration of action of the inotropic effect of the test compound are all obtained.

The compounds of the formula (I) can be administered alone but will generally be administered in admixture with a pharmaceutical carrier selected with regard to the intended route of administration and standard pharmaceutical practice. For example they may be administered orally in the form of tablets containing such excipients as starch or lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic.

For administration to man in the curative or prophylactic treatment of cardiac conditions such as congestive heart failure, it is expected that oral dosages of the compounds of the invention will be in the range from 10 mg to 1 g daily, taken in 2 to 4 divided doses per day, for an average adult patient (70 kg). Dosages for intravenous administration would be expected to be within the range 0.5 to 100 mg per single dose as required, for example in the treatment of acute heart failure. Thus for a typical adult patient, individual tablets or capsules might contain 2.5 to 250 mg of active compound, in a suitable pharmaceutically acceptable vehicle or carrier. Variations may occur depending on the weight and condition of the subject being treated as will be known to medical practitioners.

Thus the present invention provides a pharmaceutical composition comprising a compound of the formula (I) as defined above or pharmaceutically acceptable salt thereof, together with a pharmaceutically acceptable diluent or carrier.

The invention also provides a method of stimulating the heart of an animal, including a human being, which comprises administering to the animal a compound of formula (I) or pharmaceutically acceptable salt thereof, or a pharmaceutical composition as defined above, in an amount sufficient to stimulate the heart of the animal.

The invention yet further provides a compound of the formula (I) or pharmaceutically acceptable salt thereof, for use in medicine, in particular for use in stimulating the heart of a human being suffering from congestive heart failure.

DETAILED DESCRIPTION OF THE INVENTION

The compounds of the formula (I) can be prepared by a number of routes, including the following:

Route A

This route can be illustrated in general terms as follows:

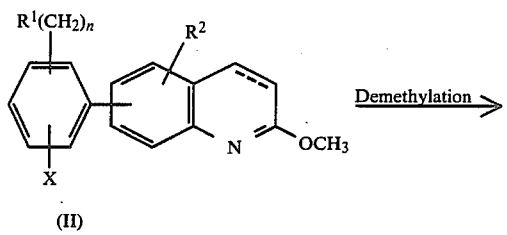

(II)

Demethylation →

Compounds (I) where $R^3$ = H.

$R^1$, $R^2$, X, n and the dotted line are as defined for formula (I). The demethylation is preferably carried out by heating the methoxyquinoline (II) either in aqueous mineral acid, typically in aqueous HCl or HBr and preferably in 48% HBr or 5 or 6M HCl, or in ethanol containing a catalytic quantity (generally 5-15% by volume) of 48% aqueous HBr, at up to reflux temperature for 0.5-8 hours. The product can then be isolated and purified by conventional procedures.

In cases where $R^1$ is an alkoxycarbonyl group (e.g. —COOCH$_3$), the demethylation may convert this to —COOH, in which case the carboxyl group can be re-esterified conventionally using, e.g., methanol in sulphuric acid.

Typical reactions are illustrated as follows:

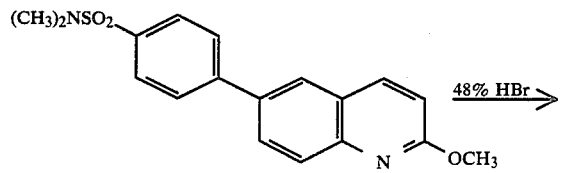

48% HBr →

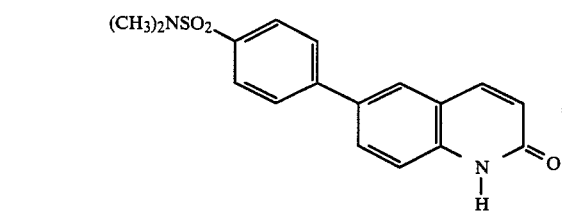

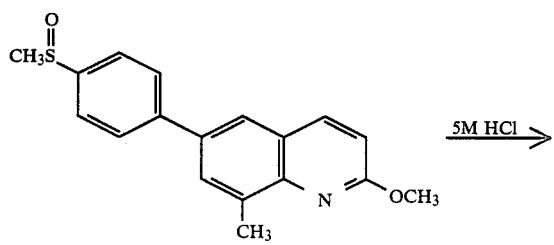

5M HCl →

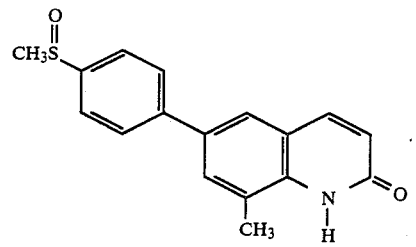

The novel starting materials of the formula (II) can be prepared by conventional procedures. These compounds form a part of the present invention.

In general terms these intermediates can be obtained as follows:

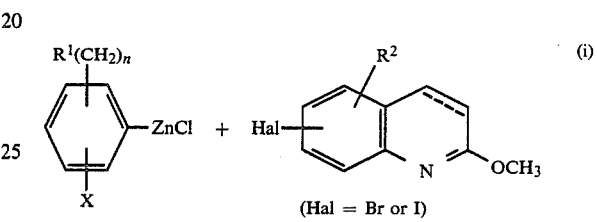

(Hal = Br or I)

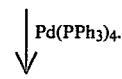 Pd(PPh$_3$)$_4$.

Compounds (II);

or

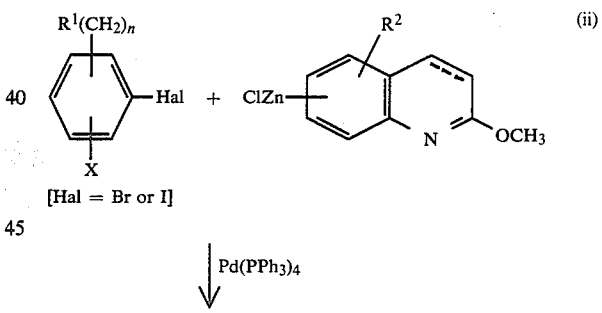

[Hal = Br or I]

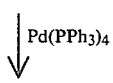 Pd(PPh$_3$)$_4$

Compounds (II).

In both cases, the reactants are typically heated at up to the reflux temperature in a suitable organic solvent such as tetrahydrofuran for, typically, 1-48 hours. The intermediates can then be isolated and if necessary purified by conventional techniques. For further experimental details see the relevant Preparations. The aryl or heteroaryl zinc chlorides can be conventionally obtained by the reaction of the corresponding bromo compound with n- or t-butyllithium and then with anhydrous zinc chloride. Tetrahydrofuran is a suitable solvent for these reactions, which should be carried out at low temperature.

Typical examples of the preparation of these intermediates are as follows:

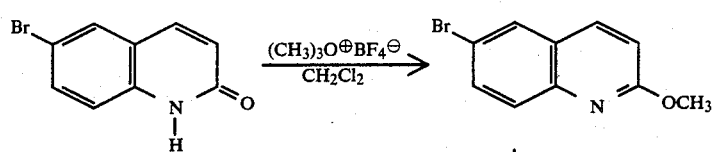
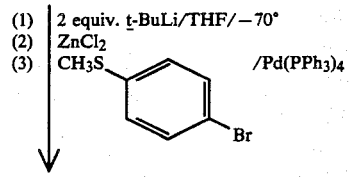
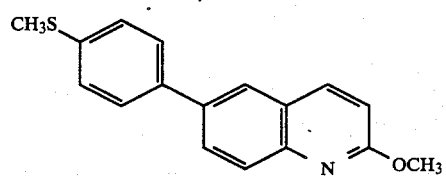
(a)
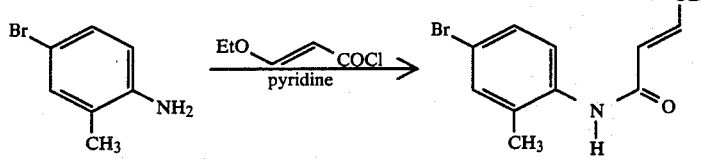
(b)
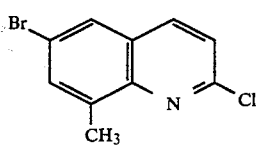  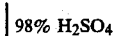 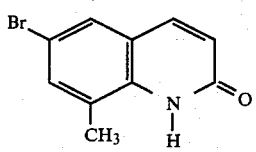
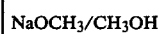
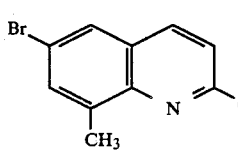 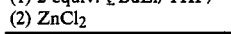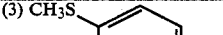 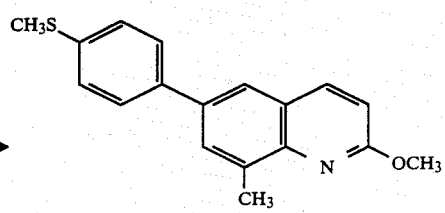
and
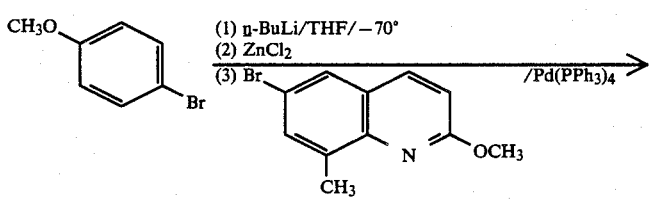 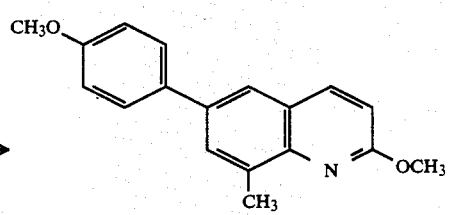
(c)
Route B
Compounds in which there is a hydroxy substituent on the phenyl ring can be prepared by the demethylation of the corresponding $C_1$–$C_4$ alkoxy compounds using conventional demethylation reagents such as aqueous mineral acid (preferably 48% aqueous HBr), boron tribromide or pyridinium hydrobromide. It is preferable to use aqueous mineral acid at up to reflux temperature.

When aqueous mineral acid is used, then this method can be essentially combined in one step with Route A, e.g. in the following manner:

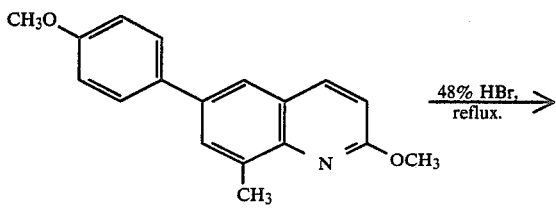

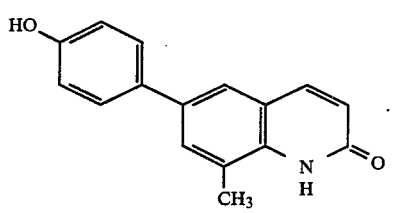

Route C

This route can be illustrated in general terms as follows:

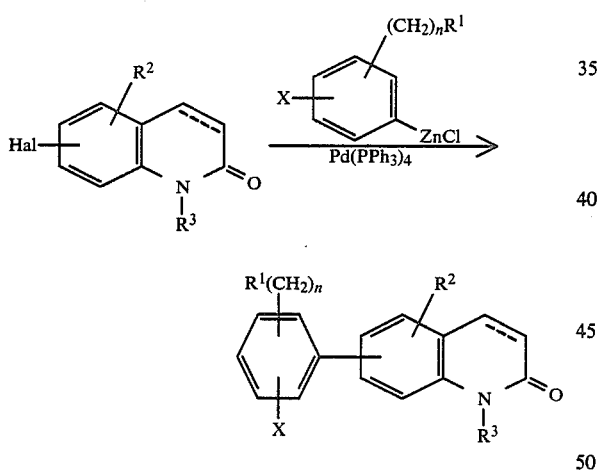

"Hal" is Br or I. Thus it will be seen that the reaction involves the displacement of the leaving group "Hal" by the aryl zinc chloride with tetrakis(triphenylphosphine)palladium (O) catalysis. The reaction is typically carried out by heating the reactants at up to reflux temperature in a suitable organic solvent, e.g. THF.

A typical reaction is illustrated as follows:

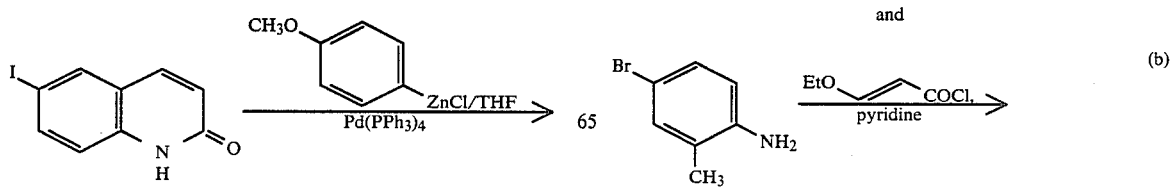

-continued

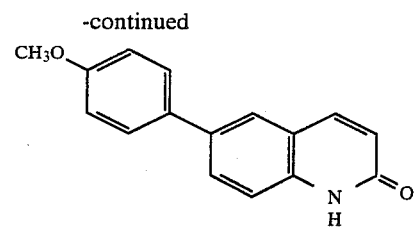

Aryl magnesium chlorides can also be used in place of zinc chlorides using other suitable transition metal catalysts (e.g. nickel based).

The starting materials are either known compounds or are obtainable conventionally.

The aryl zinc chlorides are most conveniently obtained in situ by reacting the appropriate halo benzene derivative at from −70° to 0° C. in THF with n-butyl or t-butyl lithium to obtain the lithio-derivative, followed by reaction of the lithio derivative with a solution of anhydrous zinc chloride in THF. The aryl zinc chlorides can also be prepared from the corresponding Grignard reagents by reaction with a solution of zinc chloride in THF. The desired end product can then be obtained by allowing the reaction mixture to warm to room temperature, followed by adding the appropriate halo-quinolone and the tetrakis(triphenylphosphine) palladium(O) in THF and then heating under reflux until the reaction is complete (e.g. in 1 to 48 hours). The product can then be recovered and purified conventionally.

The halo-quinolone starting materials of this route can also be prepared by conventional procedures. Typical routes to these materials, many of which are illustrated in detail in the following Preparations, are as follows:

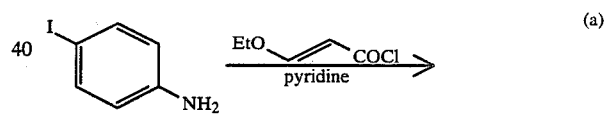
(a)

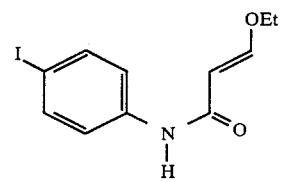

↓ 98% H₂SO₄

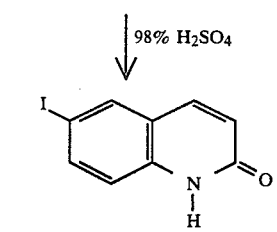

and

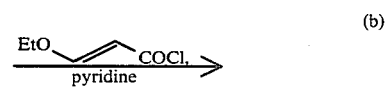
(b)

-continued

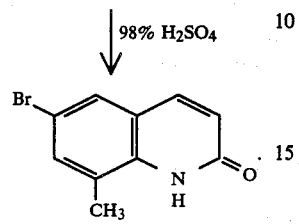

↓ 98% H2SO4

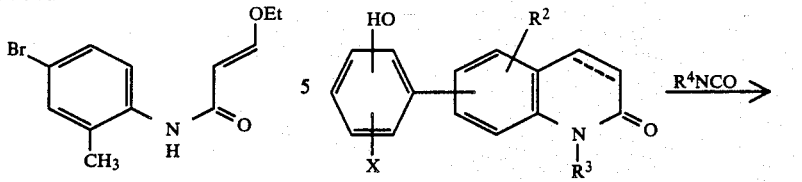

$R^4$ is a $C_1$–$C_4$ alkyl group.

Thus the reaction involves conversion of the phenolic hydroxyl group to an N-alkylcarbamoyloxy group using a $C_1$–$C_4$ alkyl isocyanate. The reaction is typically carried out in a suitable organic solvent such as THF at

Route D

This route can be illustrated in general terms as follows:

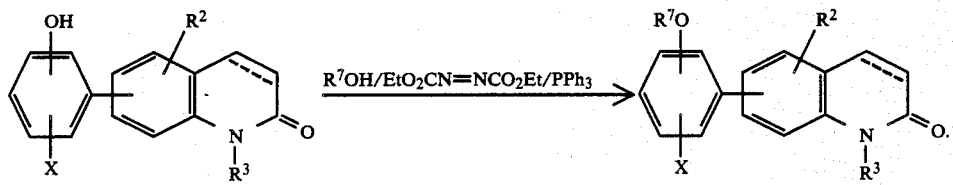

where $R^7$ is $C_1$–$C_4$ alkyl, —CH$_2$CH$_2$N($C_1$ or $C_2$ alkyl)$_2$ or HetCH$_2$—.

Thus the reaction involves alkylation of the phenolic hydroxyl group in the presence of triphenyl phosphine and diethylazodicarboxylate. The reaction is typically carried out in an inert organic solvent (e.g. THF) at up to the reflux temperature. The product can then be purified conventionally.

A typical reaction is illustrated as follows:

up to reflux temperature. The products can then be purified conventionally.

A typical reaction is illustrated as follows:

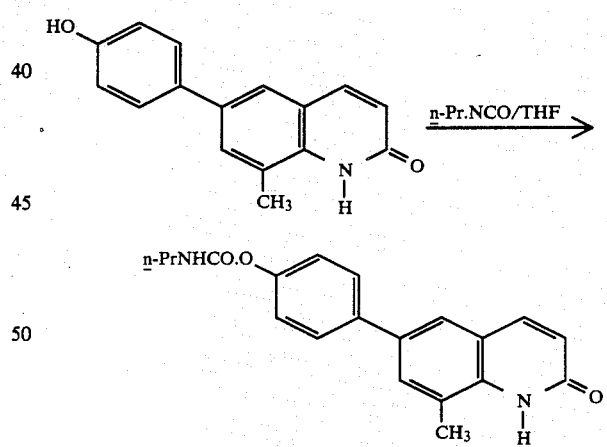

Route F

This route can be illustrated in general terms as follows:

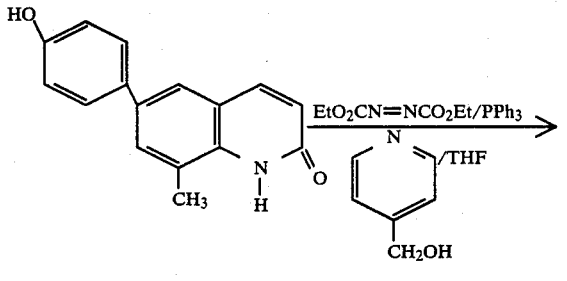

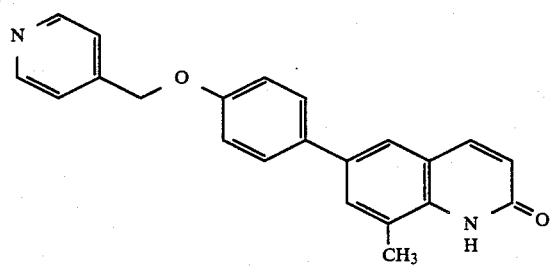

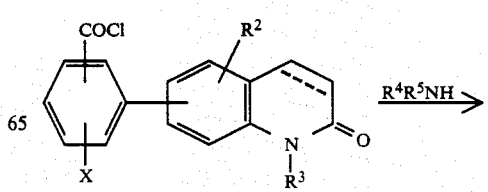

Route E

This route can be illustrated in general terms as follows:

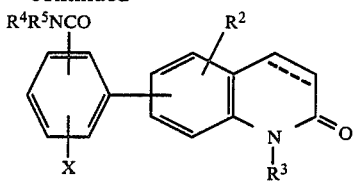

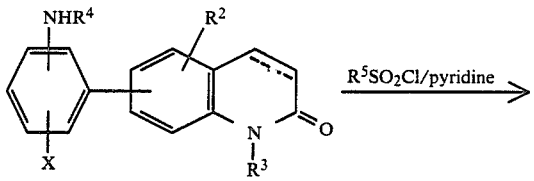

The acid chlorides are typically obtained by alkaline hydrolysis of the corresponding $C_1$–$C_4$ alkyl esters followed by conversion of the resulting carboxylic acid salt (e.g. the sodium salt) to the acid chloride by treatment with thionyl chloride. Reaction of the crude acid chloride with ammonia or the appropriate amine then yields the desired end products which can be isolated and purified conventionally.

A typical reaction is illustrated as follows:

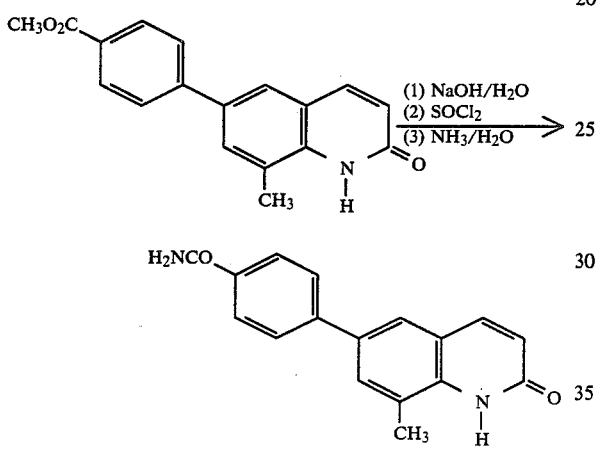

Thus the reaction involves conversion of an aniline derivative into the corresponding alkyl sulphonamide derivative with the appropriate alkyl sulphonyl chloride. The reaction is typically carried out in a suitable organic base such as pyridine at 0° to room temperature. The product can then be purified conventionally.

A typical reaction is illustrated as follows:

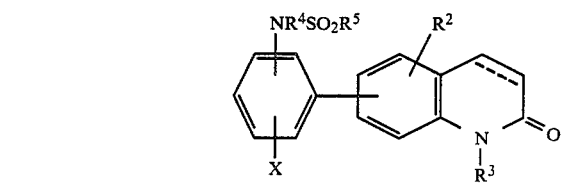

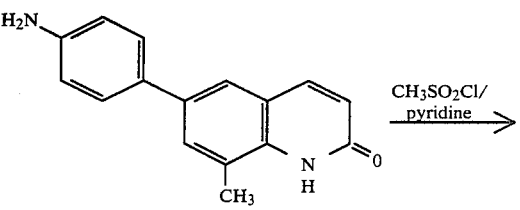

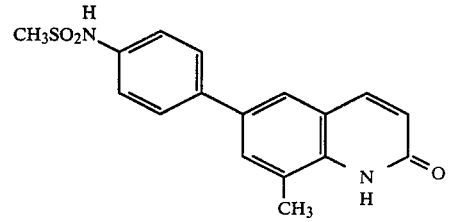

Route G

Compounds in which m is 1 or 2 can be prepared by the oxidation of the corresponding compounds in which m is zero using the appropriate quantity of oxidizing agent. The preferred oxidising agents are peracid oxidising agents such as m-chloroperbenzoic acid.

Route H

Compounds having a single bond in the 3,4-position can be obtained by the hydrogenation of the corresponding compounds having a double bond in the 3,4-position according to conventional techniques, e.g. using $H_2$ over Pd/C. Typically the reaction is carried out in an organic solvent such as ethanol at 25°–100° C. and under 15–5000 psi hydrogen pressure over palladised charcoal until the reaction is complete.

Route I

Compounds in which $R^3$ is a $C_1$–$C_4$ alkyl group can be prepared by the N-alkylation of the corresponding compounds in which $R^3$ is H. e.g. by reacting the quinoline starting material with sodium hydride or other strong base to form the anion, followed by reaction with a $C_1$–$C_4$ alkyl halide or di($C_1$–$C_4$ alkyl)sulphate in a conventional manner.

Route J

This route can be illustrated in general terms as follows:

Salts of the compounds of the formula (I) are preparable by entirely conventional methods, e.g. by reacting a solution of the compound (I) in an organic solvent with a solution of an appropriate acid in an organic solvent to form an acid addition salt, or by reacting the compound (I) with an appropriate base, e.g. an alkali metal or alkaline earth metal hydroxide, preferably aqueous sodium hydroxide, to form a pharmaceutically acceptable metal salt.

Where the compounds of the invention contain one or more asymmetric centres, then the invention includes the separated enantiomers and diastereoisomers or mixtures thereof. The separated forms can be obtained by conventional means.

The following examples illustrate the preparation of the compounds (I). (All temperatures are in °C.):

EXAMPLE 1

Preparation of 8-methyl-6-[4-methylsulphinylphenyl]-2-(1H)-quinoline

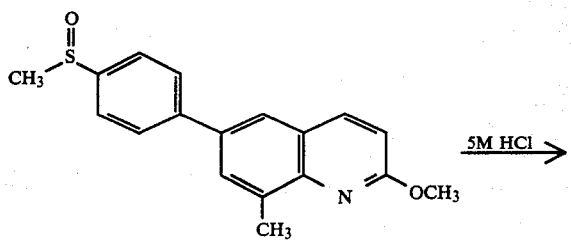

A solution of 2-methoxy-8-methyl-6-[4-methylsulphinylphenyl]-quinoline (0.86 g) in 5M hydrochloric acid (10 cm³) was heated under reflux for 3.5 hours. The cooled mixture was partitioned between aqueous 2M sodium hydroxide solution (200 cm³) and chloroform:methanol, 19:1, (100 cm³), and the aqueous phase was further extracted with chloroform:methanol, 19:1 (5×50 cm³). The combined and dried (MgSO₄) organic extracts were evaporated in vacuo and the residue was recrystallized from ethyl acetate/methanol to afford the title compound, m.p. 298°–299°, (0.29 g).

Analysis %: Found: C, 69.0; H, 5.2; N, 4.7; Calculated for $C_{17}H_{15}NO_2S$: C, 68.7; H, 5.2; N, 4.7.

EXAMPLES 2–12

The following compounds were prepared similarly to Example 1 starting from the appropriately substituted 2-methoxyquinoline and either 5M aqueous HCl (Examples 2–19), 6M aqueous HCl (Example 12) or 48% aqueous Br (Examples 10 and 11).

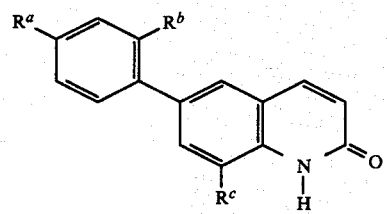

| Example No. | $R^a$ | $R^b$ | $R^c$ | Form Isolated and m.p. (°C.) | C | H | N |
|---|---|---|---|---|---|---|---|
| 2 | —SCH₃ | —H | —H | Free base, 287.5–290° | 71.8 (71.9 | 5.1 4.9 | 5.3 5.2) |
| 3 | —S(O)CH₃ | —H | —H | Free base, 294–295° | 67.7 (67.8 | 4.7 4.6 | 4.8 4.9) |
| 4 | —SO₂CH₃ | —H | —H | Free base, 326–328° | 64.0 (64.2 | 4.4 4.4 | 5.6 5.7) |
| 5 | —OCH₃ | —H | —CH₃ | Free base, 276–279° | 77.2 (77.0 | 5.8 5.7 | 5.4 5.3) |
| 6 | —SO₂NHCH₃ | —H | —CH₃ | Free base, 234–237° | 61.9 (62.2 | 4.9 4.9 | 8.5 8.5) |
| 7 | —SO₂NH₂ | —H | —CH₃ | Free base, 306–310° | 61.0 (61.1 | 4.8 5.0 | 9.0 8.9) |
| 8 | —NH₂ | —H | —H | Monohydrochloride 0.25 H₂O, >300° | 65.3 (65.0 | 4.8 4.9 | 10.4) 10.1) |
| 9 | N-methylimidazolyl | —H | —H | Monohydrochloride 0.25 H₂O, >350° | 65.4 (65.9 | 4.3 4.4 | 12.8 12.8) |
| 10 | —H | —SO₂N(CH₃)₂ | —H | Free base 0.25 H₂O, 278–280° | 61.0 (61.3 | 5.1 5.0 | 8.5 8.4) |
| 11 | —SO₂N(CH₃)₂ | —H | —H | Free base, 286–288° | 61.8 (62.2 | 4.9 4.9 | 8.3 8.5) |
| 12 | —NH₂ | —H | —CH₃ | Free base, 208–211° | Characterised by ¹H N.m.r. | | |

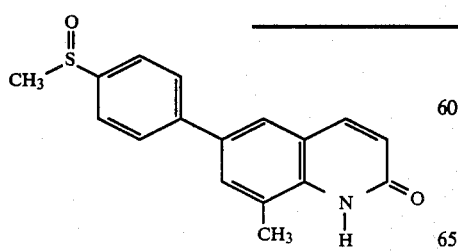

EXAMPLE 13

6-[4-Methoxycarbonylphenyl]-2-(1H)-quinolone ¼ hydrate and 6-[4-carboxyphenyl]-2-(1H)-quinolone disodium salt dihydrate Part A

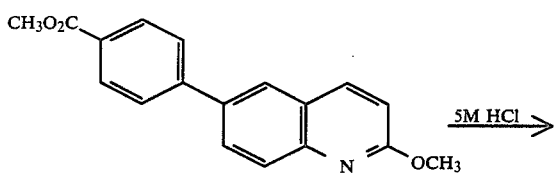

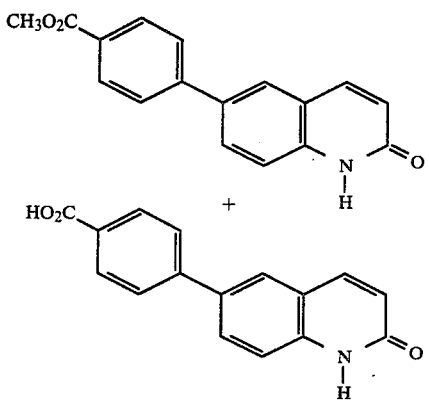

A suspension of 2-methoxy-6-[4-methoxycarbonylphenyl]quinoline (6.71 g) in 5M HCl (150 cm³) was warmed at 100° for 6 hours. The cooled solution was filtered and dried to afford a solid (6.43 g). A small quantity (0.63 g) of this solid material was suspended in chloroform:methanol, 2:1 (5 cm³), and treated with 2M sodium hydroxide solution (2 cm³). After warming for 10 minutes at 100° the mixture was filtered and the filtrate was concentrated in vacuo to 2 cm³ volume to afford, on cooling, 6-[4-methoxycarbonylphenyl]-2-(1H)-quinolone ¼ hydrate, m.p. >325°, (0.1 g).

Analysis %: Found: C, 72.1; H, 4.6; N, 5.0; Calculated for C₁₇H₁₃NO₃.¼H₂O: C, 72.0; H, 4.8; N, 4.9.

Part B

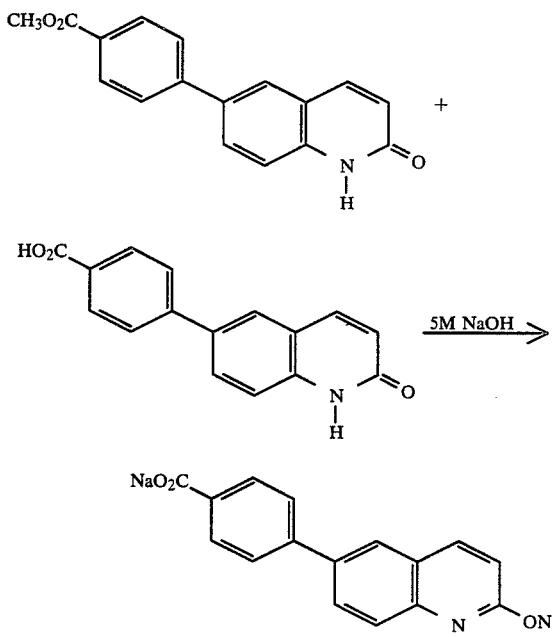

The remainder of the solid material from Part A was heated under reflux in 5M sodium hydroxide (90 cm³) for 16 hours. The cooled solution was then filtered to give 6-[4-carboxyphenyl]-2-(1H)-quinolone disodium salt dihydrate, m.p. >300° (4.66 g).

Analysis %: Found: C, 56.0; H, 3.6; N, 4.2; Calculated for C₁₆H₉NO₃.2Na.2H₂O: C, 55.7; H, 3.8; N, 4.1.

EXAMPLE 14

Part A

8-Methyl-6-[4-methoxycarbonylphenyl]-2-(1H)-quinolone. 0.5H₂O, m.p. 293°, was prepared similarly to Example 13(A) using 2-methoxy-8-methyl-6-(4-methoxycarbonylphenyl)quinoline and 5M HCl.

Analysis %: Found: C, 71.4; H, 5.4; N, 4.4; Calculated for C₁₈H₁₅NO₃.½H₂O: C, 71.5; H, 5.3; N, 4.6.

Part B

8-Methyl-6-[4-carboxyphenyl]-2-(1H)-quinolone disodium salt, 1.75 H₂O, m.p. >300°, was prepared similarly to Example 13(B) by reacting a mixture of 8-methyl-6-(4-methoxycarbonylphenyl)-2-(1H)-quinolone and its 6-(4-carboxyphenyl) analogue with 5M sodium hydroxide.

Analysis %: Found: C, 57.6; H, 4.5; N, 4.0; Calculated for C₁₇H₁₁NO₃.2Na.1.75H₂O: C, 57.6; H, 4.1; N, 4.0.

EXAMPLE 15

Preparation of
8-methyl-6-[4-hydroxylphenyl]-2-(1H)-quinolone

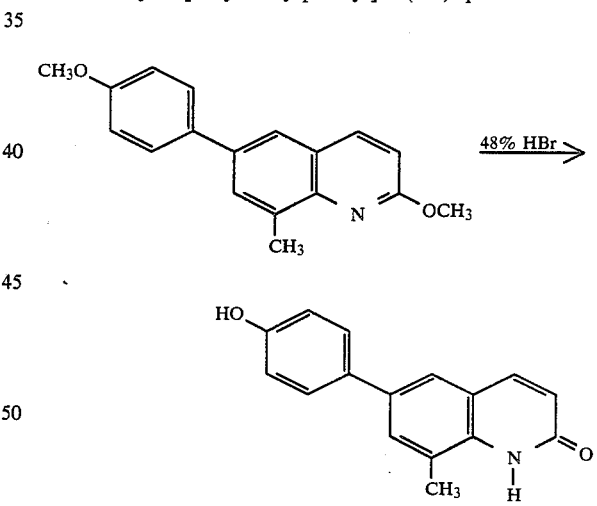

A mixture of 2-methoxy-8-methyl-6-[4-methoxyphenyl]quinoline (4.82 g) and 48% aqueous HBr (100 cm³) was heated under reflux for 6 hours. The cooled mixture was diluted with water (200 cm³), the solid filtered off, and dissolved in chloroform:methanol, 4:1 (500 cm³). The organic phase was washed with water (2×25 cm³), dried (MgSO₄) and evaporated in vacuo to give a solid which was recrystallised from propan-2-ol to afford the title compound, m.p. 270°-274°, (2.5 g).

Analysis %: Found: C, 76.4; H, 5.3; N, 5.7; Calculated for C₁₆H₁₃NO₂: C, 76.5; H, 5.2; N, 5.6.

EXAMPLE 16

Preparation of 6-[4-methoxyphenyl]-2-(1H)-quinolone

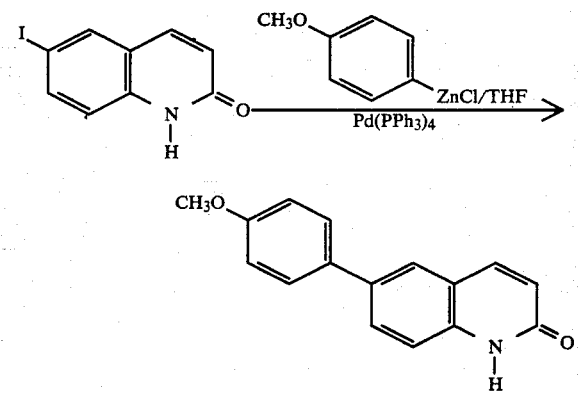

A solution of t-butyl lithium (9.0 cm³ of a 2.0M solution in n-pentane) was added at −70° to a stirred solution of 4-bromoanisole (1.13 cm³) in tetrahydrofuran (THF) (20 cm³) under nitrogen. After 10 minutes a solution of anhydrous zinc chloride (1.23 g) in THF (10 cm³) was added and the mixture was allowed to warm to room temperature over 0.5 hour. A mixture of 6-iodo-2-(1H)-quinolone (0.813 g) and tetrakis(triphenylphosphine) palladium (0) (0.03 g) was added and the mixture was heated under reflux for 2 hours. Volatile material was then removed in vacuo and the residue was partitioned between chloroform:methanol, 9:1 (100 cm³) and a solution of ethylenediaminetetraacetic acid disodium salt (7 g) in water (100 cm³). The aqueous phase was further extracted with chloroform:methanol, 9:1 (3×100 cm³), and the combined and dried (MgSO₄) organic extracts were evaporated to give an oily solid which was triturated with ethyl acetate. Recrystallization of the residue from ethyl acetate-methanol-chloroform afforded the title compound, m.p. 262°–264° (0.359 g).

Analysis %: Found: C, 76.3; H, 5.2; N, 5.6; Calculated for $C_{16}H_{13}NO_2$: C, 76.5; H, 5.2; N, 5.6.

EXAMPLE 17

Preparation of 8-methyl-6-[4-(4-pyridylmethoxy)phenyl]-2-(1H)-quinolone

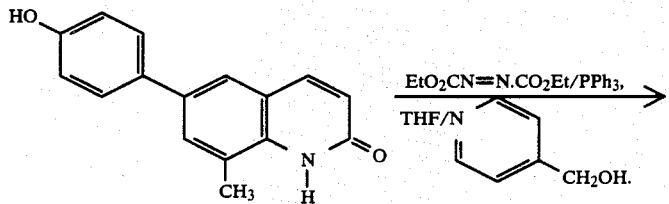

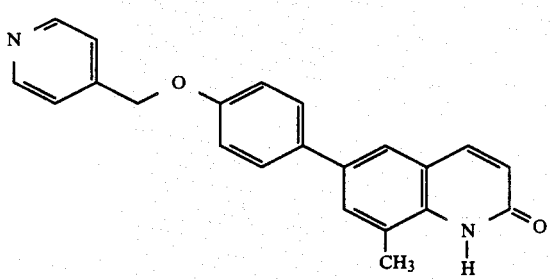

A solution of diethylazodicarboxylate (0.189 cm³) in THF (5 cm³) was added at room temperature to a stirred suspension of 8-methyl-6-[4-hydroxyphenyl]-2-(1H)-quinolone (0.25 g), 4-hydroxymethylpyridine (0.109 g) and triphenylphosphine (0.315 g) in THF (10 cm³) under nitrogen. The mixture was heated under reflux for 18 hours, silica (10 g) (Merck "MK 60.9385" [Trade Mark]) was added and volatile material was removed in vacuo. The residue was placed on top of a silica column (Merck "MK 60.9385" [Trade Mark]) and eluted with ethyl acetate:methanol, 9:1. Combination and evaporation of the appropriate fractions in vacuo gave a solid (0.24 g) which was recrystallised from ethyl acetate-methanol to afford the title compound, m.p. 270.5°–273.5°, (0.08 g).

Analysis %: Found: C, 76.9; H, 5.4; N, 8.1; Calculated for $C_{22}H_{18}N_2O_2$: C, 77.2; H, 5.3; N, 8.2.

EXAMPLE 18

8-Methyl-6-[4-(2-dimethylaminoethoxy)phenyl]-2-(1H)-quinolone, m.p. 216° (decomp.), was prepared similarly to the previous Example using 8-methyl-6-[4-hydroxyphenyl]-2-(1H)-quinolone, diethylazodicarboxylate, triphenylphosphine and 2-dimethylaminoethanol as the starting materials.

EXAMPLE 19

Preparation of 8-methyl-6-[4-(N-n-propylcarbamoyloxy)phenyl]-2-(1H)-quinolone

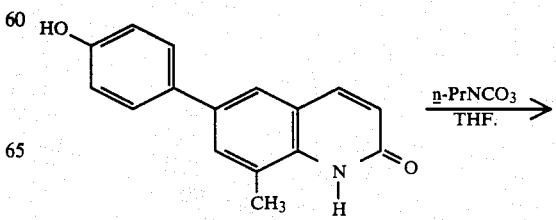

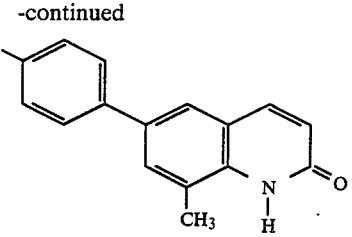

A solution of 8-methyl-6-[4-hydroxyphenyl]-2-(1H)-quinolone (0.30 g) and n-propylisocyanate (0.5 cm³) was heated under reflux in THF (10 cm³) under nitrogen for 50 hours. Methanol (10 cm³) was then added to dissolve solid material, followed by silica (Merck "MK 60.9385" [Trade Mark]) (10 g), and the volatile material was removed in vacuo. The residue was placed on top of a silica column (Merck "MK 60.9385") and eluted with chloroform:methanol, 19:1. Combination and evaporation of appropriate fractions in vacuo gave a solid which was recrystallised from propan-2-ol to afford the title compound, m.p. 224°–228°, (0.28 g).

Analysis %: Found: C, 71.5; H, 6.3; N, 8.4; Calculated for $C_{20}H_{20}N_2O_3$: C, 71.4; H, 6.0; N, 8.3.

EXAMPLE 20

Preparation of 6-[4-carbamoylphenyl]-2-(1H)-quinolone, $0.25H_2O$

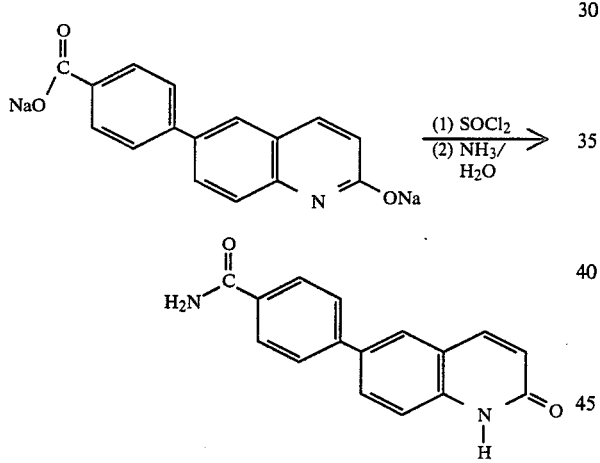

A suspension of 6-[4-carboxyphenyl]-2-(1H)-quinolone disodium salt dihydrate (0.5 g) (see Example 13B) in thionyl chloride (10 cm³) was heated under reflux for 10 minutes. The cooled solution was evaporated in vacuo to afford a yellow solid which was treated without purification with aqueous ammonia solution (5 cm³, S.G. 0.88) with stirring. The solid material was filtered off and warmed with chloroform:methanol, 4:1, to remove soluble impurities and the remaining solid was filtered to afford the title compound, m.p. >320°, (0.3 g).

Analysis %: Found: C, 71.5; H, 4.5; N, 10.4; Calculated for $C_{16}H_{12}N_2O_2 \cdot 0.025H_2O$: C, 71.5; H, 4.7; N, 10.4.

EXAMPLES 21–23

The following compounds were prepared similarly to the previous example using 6-[4-carboxyphenyl]-2-(1H)-quinolone disodium salt dihydrate (Examples 21 and 22 or 8-methyl-6-[4-carboxyphenyl]-2-(1H)-quinolone disodium salt 1.75 hydrate (Example 23), and ammonia or the appropriately substituted amine as the starting materials:

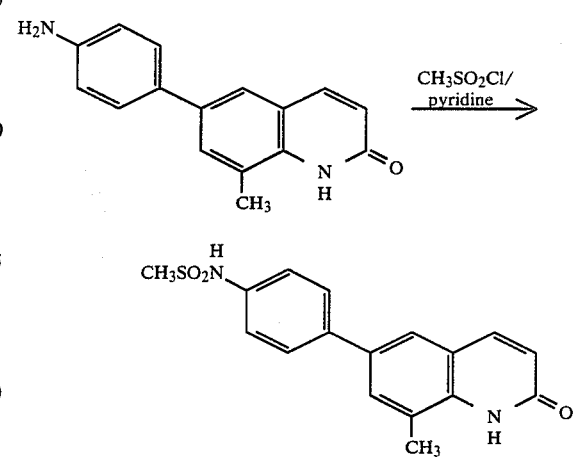

| Example No. | $R^d$ | $R^e$ | Form Isolated and m.p. (°C.) | Analysis % (Theoretical in brackets) C | H | N |
|---|---|---|---|---|---|---|
| 21 | —N(CH₃)₂ | —H | Free base, 268–270° | 73.6 (74.0 | 5.4 5.5 | 9.6 9.6) |
| 22 | CH₃<br>\|<br>—NCH₂CH₂N(CH₃)₂ | —H | Free base, 210–212° | 72.1 (72.2 | 6.6 6.6 | 11.9 12.0) |
| 23 | —NH₂ | —CH₃ | Free base 0.5 H₂O, >300° | 71.1 (71.1 | 5.0 5.2 | 10.2 9.8) |

EXAMPLE 24

Preparation of 8-Methyl-6-(4-methylsulphonamidophenyl)-2-(1H)-quinolone, $0.25H_2O$ Methanesulphonyl chloride (0.15 cm³) was added dropwise to a stirred solution of 8-methyl-6-(4-aminophenyl)-2-(1H)-quinolone (0.47 g) (see Example 13) in pyridine (3 cm³) at room temperature. After 0.5 hours volatile material was removed in in vacuo and the residue was partitioned between water (50 cm³) and dichloromethane:methanol, 4:1 (50 cm³). The insoluble material was filtered off, washed with methanol (10 cm³) and dried to afford the title compound, m.p. 340°–343° (0.45 g).

Analysis %: Found: C, 61.3; H, 5.0; N, 8.5; Calculated for $C_{17}H_{16}N_2O_3S \cdot 0.25H_2O$: C, 61.3; H, 5.0; N, 8.4.

The following preparations illustrate the synthesis of certain starting materials. All temperatures are in °C.:

PREPARATION 1

2-Methoxy-6-[4-methoxycarbonylphenyl]quinoline

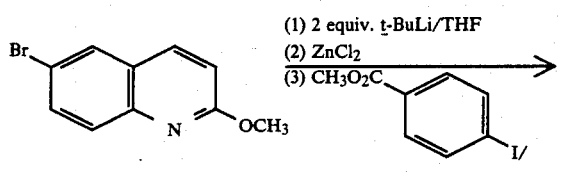

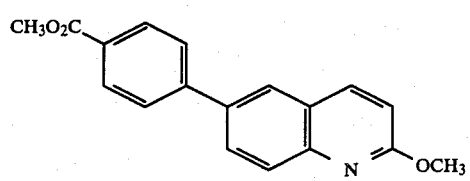

t-Butyllithium (30 cm³ of a 2.0M solution in n-pentane) was added dropwise at −70° to a stirred solution of 6-bromo-2-methoxyquinoline (7.14 g) in tetrahydrofuran (THF) (50 cm³) under nitrogen. After 10 minutes a solution of anhydrous zinc chloride (4.09 g) in THF (30 cm³) was added and the solution was allowed to warm to room temperature. A mixture of methyl 4-iodobenzoate (7.8 g) and tetrakis(triphenylphosphine)-palladium (0) (0.32 g) was added and the mixture was heated under reflux for 1 hour. Volatile material was removed in vacuo and the residue was partitioned between chloroform (150 cm³) and a solution of ethylenediaminetetraacetic acid disodium salt (22.4 g) in water (400 cm³). The aqueous phase was further extracted with chloroform (2×100 cm³), and the combined and dried (MgSO₄) organic extracts were evaporated to give a solid which was recrystallised from acetone to afford the title compound, m.p. 158°–161°, (6.81 g).

Analysis %: Found: C, 74.1; H, 5.1; N, 4.6; Calculated for $C_{18}H_{15}NO_3$: C, 73.7; H, 5.1; N, 4.8.

PREPARATIONS 2–10

The following compounds were prepared similarly to Preparation 1 using the appropriately substituted halobenzene derivative and either 6-bromo-2-methoxyquinoline (Preparations 2–5), or 6-bromo-8-methyl-2-methoxyquinoline (Preparations 6–10) as the starting materials.

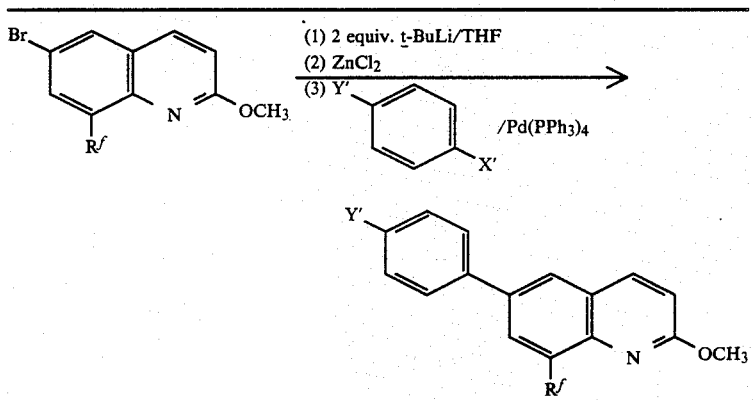

| Preparation No. | R$^f$ | X' | Y' | Form Isolated and m.p. (°C.) | Analysis % (Theoretical in brackets) | | |
|---|---|---|---|---|---|---|---|
| | | | | | C | H | N |
| 2 | —H | —Br | —SO₂N(CH₃)₂ | Free base, 174–177° | 62.3 (63.1) | 5.2 (5.3) | 8.1 (8.2) |
| 3 | —H | —Br | —SCH₃ | Free base, 151–153° | 72.5 (72.6) | 5.4 (5.4) | 5.0 (5.0) |
| 4 | —H | —Br | —N⟨pyrrolyl⟩ | Free base, 0.25 H₂O, 175–178° | 74.5 (74.6) | 5.1 (5.1) | 13.8 (13.7) |
| 5* | —H | —I | —NH₂ | Free base, 159–161° | 76.9 (76.8) | 5.7 (5.6) | 11.2 (11.2) |
| 6* | —CH₃ | —I | —SO₂NH₂ | Free base, 215–6° | 61.5 (62.2) | 4.9 (4.9) | 8.7 (8.5) |
| 7 | —CH₃ | —I | —CO₂CH₃ | Free base, 142° | 74.1 (74.2) | 5.5 (5.6) | 4.4 (4.6) |
| 8 | —CH₃ | —Br | —SCH₃ | Free base, 99.5–103° | 73.1 (73.2) | 5.8 (5.8) | 4.7 (4.7) |
| 9* | —CH₃ | —Br | —SO₂NHCH₃ | Free base, 140–143.5° | 62.9 (63.1) | 5.3 (5.3) | 7.8 (8.2) |
| 10* | —CH₃ | —I | —NH₂ | Free base, 145–8° | 76.5 (76.0) | 6.4 (6.2) | 10.0 (10.4) |

*These Preparations require the use of two equivalents of the quinolylzinc chloride reagent per mole of the substituted halobenzene derivative.

PREPARATION 11

2-Methoxy-8-methyl-6-[4-methoxyphenyl]quinoline

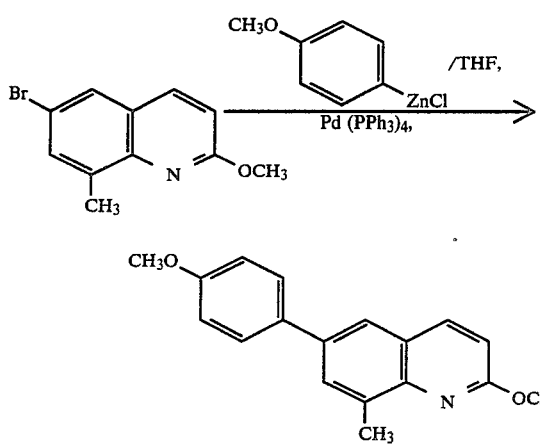

n-Butyllithium (33.3 cm³ of a 1.5M solution in n-hexane) was added dropwise at −70° to a stirred solution of 4-bromoanisole (6.26 cm³) in THF (70 cm³) under nitrogen. After ten minutes, a solution of anhydrous zinc chloride (6.814 g) in THF (50 cm³) was added and the mixture was allowed to warm to room temperature over 0.5 hour. A mixture of 6-bromo-2-methoxy-8-methylquinoline (12.8 g) and tetrakis(triphenylphosphine)palladium (0) (0.5 g) was added and the mixture heated under reflux for 2 hours. Volatile material was removed in vacuo and the residue was partitioned between chloroform (150 cm³) and a solution of ethylenediaminetetraacetic acid (40 g) in water (250 cm³). The organic layer was dried (MgSO₄) and evaporated to afford an oil which was chromatographed on silica (Merck "MK 60.9385" [Trade Mark]) eluting with hexane:ethyl acetate, 19:1. Combination and evaporation of the appropriate fractions afforded the title compound (5.49 g). A small portion of this was recrystallised from methanol and had m.p. of 104°–106° and the following analysis:

Analysis %: Found: C, 77.4; H, 6.3; N, 5.2; Calculated for $C_{18}H_{17}NO_2$: C, 77.4; H, 6.1; N, 5.0.

PREPARATION 12

The following compound was prepared similarly to the previous Preparation using 6-bromo-2-methoxyquinoline and the appropriate phenyl zinc chloride derivative in the presence of tetrakis(triphenylphosphine)palladium (0):

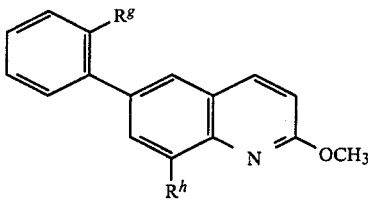

| Preparation No. | $R^g$ | $R^h$ | Form Isolated and m.p. (°C.) | Analysis % (Theoretical in brackets) | | |
|---|---|---|---|---|---|---|
| | | | | C | H | N |
| 12* | —SO₂N(CH₃)₂ | —H | Free base, | 63.1 | 5.3 | 8.3 |
| | | | 145–147° | (63.1 | 5.3 | 8.2) |

*The lithio-derivative of N,N—dimethylbenzenesulphonamide was prepared by the ortho-metallation of N,N—dimethylbenzenesulphonamide in THF at 0° with n-butyllithium (1.5 M solution in n-hexane). The corresponding zinc chloride derivative was then prepared by reaction with anhydrous zinc chloride in THF.

PREPARATION 13

2-Methoxy-6-[4-methylsulphinylphenyl]quinoline

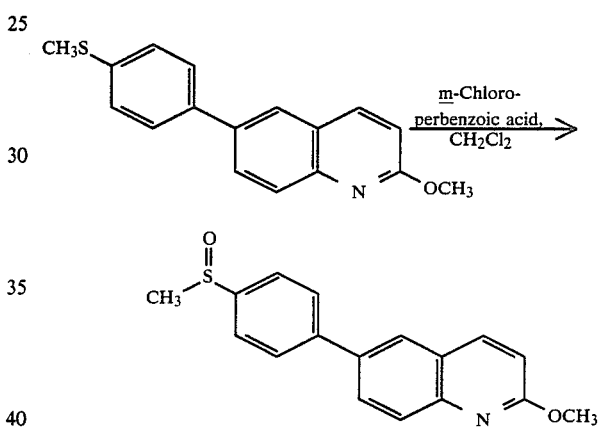

A solution of m-chloroperbenzoic acid (0.56 g) in dichloromethane (5 cm³) was added dropwise at −70° to a stirred solution of 2-methoxy-6-[4-methylthiophenyl]quinoline (0.7 g) in dichloromethane (10 cm³). The mixture was warmed to room temperature over 1 hour, taken into dichloromethane (25 cm³) and washed with sodium carbonate solution (10 cm³). The organic phase was dried (MgSO₄) and evaporated and the residue was chromatographed on silica (Merck "MK 60.9385" [Trade Mark]) eluting with chloroform:methanol, 19:1. The appropriate fractions were combined and evaporated to give a solid which was recrystallised from acetone-hexane to afford the title compound, m.p. 163.5°–165.5°, (0.55 g).

Analysis %: Found: C, 68.3; H, 5.0; N, 4.7; Calculated for $C_{17}H_{15}NO_2S$: C, 68.7; H, 5.1; N, 4.7.

PREPARATION 14

2-Methoxy-8-methyl-6-[4-methylsulphinylphenyl]-quinoline, m.p. 119.5°–121.5°, was prepared similarly to the previous Preparation using 2-methoxy-8-methyl-6-[4-methylthiophenyl]-quinoline and m-chloroperbenzoic acid as the starting materials.

Analysis %: Found: C, 68.9; H, 5.4; N, 4.6; Calculated for $C_{18}H_{17}NO_2S$: C, 69.4; H, 5.5; N, 4.5;

PREPARATION 15

2-Methoxy-6-[4-methylsulphonylphenyl]quinoline

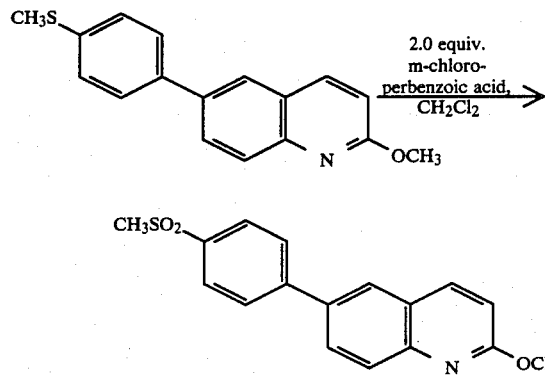

A solution of m-chloroperbenzoic acid (1.12 g) in dichloromethane (5 cm³) was added dropwise at −70° to a stirred solution of 2-methoxy-6-[4-methylthiophenyl]quinoline (0.7 g) in dichloromethane (10 cm³). The mixture was allowed to warm to room temperature over one hour and the solution was washed with saturated sodium carbonate solution (10 cm³). The organic phase was dried (MgSO₄) and evaporated in vacuo to give a solid which was recrystallised from ethyl acetate to afford the title compound, m.p. 182°-184° (0.674 g).

Analysis %: Found: C, 64.8; H, 4.8; N, 4.6; Calculated for C₁₇H₁₅NO₃S: C, 65.1; H, 4.8; N, 4.5.

PREPARATION 16

6-Bromo-2-methoxyquinoline

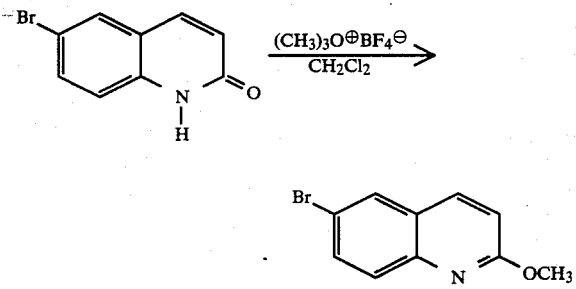

A mixture of 6-bromo-2-[1H]-quinolone (2.90 g) and trimethyloxoniumtetrafluoroborate (2.10 g) was stirred in dichloromethane (50 cm³) for 48 hours under nitrogen. Aqueous 10% sodium hydroxide (20 cm³) was added and the aqueous phase was extracted with dichloromethane (2×40 cm³). The dried (MgSO₄) extracts were evaporated and the residue was crystallised from petroleum ether (b.p. 60°-80°) to yield the title compound, m.p. 90°-94°, (2.16 g).

Analysis %: Found: C, 50.7; H, 3.5; N, 6.0; Calculated for C₁₀H₈NOBr: C, 50.4; H, 3.4; N, 5.9.

6-Bromo-2-(1H)-quinolone is a known compound.

PREPARATION 17

6-Bromo-2-methoxyquinoline (alternative to Preparation 16)

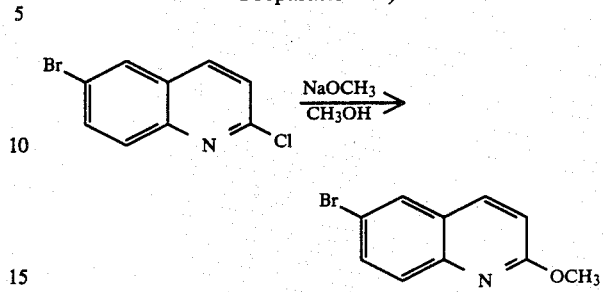

A solution of 2-chloro-6-bromoquinoline (4.0 g) in methanol (20 cm³) was heated under reflux with sodium methoxide [made from sodium (0.5 g) and methanol (20 cm³)] for 16 hours. The solvent was removed in vacuo and the residue was partitioned, between water (20 cm³) and chloroform (100 cm³). The aqueous phase was extracted wth chloroform (2×30 cm³) and the dried (MgSO₄) organic extracts were evaporated to give a solid which was recrystallised from petroleum ether (b.p. 60°-80°) to yield the title compound, m.p. 93°-96°, (3.0 g).

Analysis %: Found: C, 50.4; H, 3.4; N, 6.0; Calculated for C₁₀H₈NOBr: C, 50.4; H, 3.4; N, 5.9.

PREPARATION 18

6-Bromo-2-methoxy-8-methylquinoline, m.p. 89°-91°, was prepared similarly to the previous preparation using 6-bromo-2-chloro-8-methylquinoline and sodium methoxide as the starting materials.

6-Bromo-2-chloroquinoline is a known compound.

PREPARATION 19

Trans-N-(4-Bromo-2-methylphenyl)-3-ethoxypropenamide

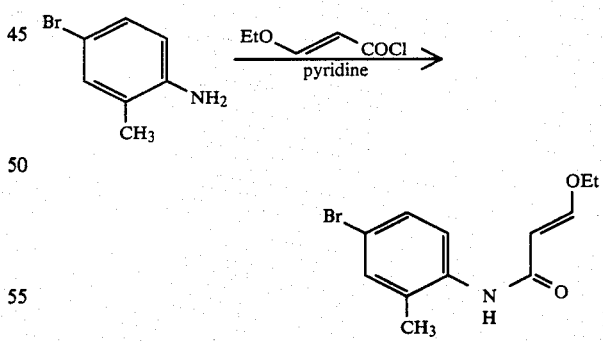

Trans-3-ethoxypropenoyl chloride (0.74 g) was added at 0° to a stirred solution of 4-bromo-2-methylaniline (0.93 g) in pyridine (10 cm³). After 0.5 hours water (40 cm³) was added, the solid material was filtered off, washed with water (30 cm³) and dried. The product was recrystallised from ethyl acetate to afford trans-N-(4-bromo-2-methylphenyl)-3-ethoxypropenamide, m.p. 163°-164°, (1.3 g).

Analysis %: Found: C, 50.7; H, 5.0; N, 5.1; Calculated for C₁₂H₁₄NO₂Br: C, 50.7; H, 5.0; N, 4.9.

PREPARATION 20

Trans-N-(4-iodophenyl)-3-ethoxypropenamide, m.p. 181°–182°, was prepared similarly to the previous Preparation using trans-3-ethoxypropenoyl chloride and 4-iodoaniline as the starting materials.

PREPARATION 21

6-Bromo-8-methyl-2-(1H-quinolone

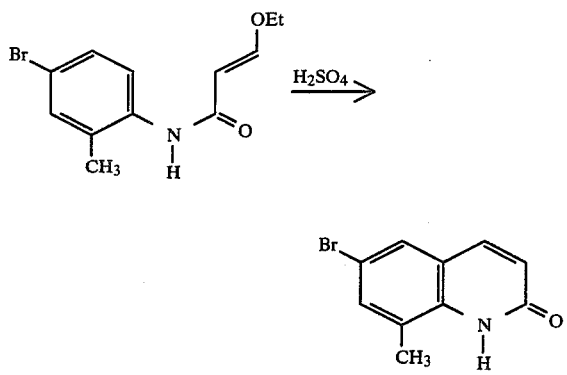

Trans-N-(4-bromo-2-methylphenyl)-3-ethoxypropenamide (2.0 g) was added portionwise with stirring to 98% sulphuric acid (15 cm³) at room temperature. After 16 hours the solution was poured onto ice (100 cm³) and the resulting precipitate was filtered off and dried (1.5 g). Recrystallisation from ethyl acetate-methanol afforded 6-bromo-8-methyl-2-(1H)-quinolone, m.p. 272°–274°.

Analysis %: Found: C, 50.4; H, 3.4; N, 6.1; Calculated for $C_{10}H_8NOBr$: C, 50.4; H, 3.4; N, 5.9.

PREPARATION 22

6-Iodo-2-(1H)-quinolone, m.p. 260°–263°, was prepared similarly to the previous Preparation using trans-N-(4-iodophenyl)-3-ethoxypropenamide and 98% sulphuric acid as the starting materials.

Analysis %: Found: C, 40.0; H, 2.2; N, 5.1; Calculated for $C_{19}H_6INO$: C, 39.9; H, 2.2; N, 5.2.

PREPARATION 23

6-Bromo-2-chloro-8-methylquinoline

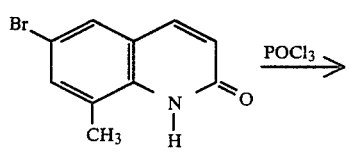

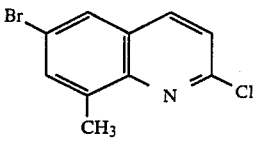

A mixture of 6-bromo-8-methyl-2-(1H)-quinolone (12.0 g) in phosphorus oxychloride (100 cm³) was heated under reflux for 2 hours. Volatile material was removed in vacuo, the residue dissolved in chloroform (200 cm³), and the resulting solution was poured onto ice (200 g). The mixture was basified with aqueous ammonia solution (S.G. 0.88) to pH10 and the aqueous phase was further extracted with chloroform (2×100 cm³). The combined and dried (MgSO₄) extracts were concentrated in vacuo to give a solid (10.7 g) which was recrystallised from ethanol to afford 6-bromo-2-chloro-8-methyl-quinoline, m.p. 114°–116°.

Analysis %: Found: C, 47.2; H, 2.7; N, 5.8; Calculated for $C_{10}H_7BrClN$: C, 46.8; H, 2.7; N, 5.5.

We claim:

1. A compound of the formula:

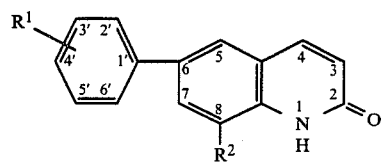

or a pharmaceutically acceptable salt thereof, wherein $R^1$ is —NH₂, —NHSO₂(C₁-C₄alkyl), —S(O)$_m$(C₁-C₄alkyl) where m is zero, one or two, —SO₂NH₂, —SO₂NH(C₁-C₄alkyl), —SO₂N(C₁-C₄alkyl)₂, —OCONH(C₁-C₄alkyl), —OH, —O(C₁-C₄alkyl), —OCH₂CH₂N(C₁-C₂alkyl)₂, —OCH₂(pyridyl), —COOH, —COO(C₁-C₄alkyl), —CONH₂, —CON(C₁-C₄alkyl)₂, —CON(C₁-C₄alkyl)CH₂CH₂N(C₁-C₂alkyl)₂ or imidazol-1-yl, said $R^1$ being attached to the 2'- or 4'-positions of the benzene ring; and $R^2$ is hydrogen or methyl.

2. A compound as claimed in claim 1 wherein $R^1$ is —NH₂, —NHSO₂CH₃, —S(O)$_m$CH₃ where m is zero, one or two, —SO₂NH₂, —SO₂NHCH₃, —SO₂N(CH₃)₂, —OCONH(n-propyl), —OH, —OCH₃, —OCH₂CH₂N(CH₃)₂, —OCH₂(4-pyridyl), —COOH, —COOCH₃, —CONH₂, —CON(CH₃)₂, —CON(CH₃)CH₂CH₂N(CH₃)₂ or imidazol-1-yl.

3. A compound as claimed in claim 2 wherein $R^1$ is attached to the 4'-position of the benzene ring.

4. 8-Methyl-6-[4-methylsulphinylphenyl]-2-(1H)-quinolone.

5. 8-Methyl-6-[4-hydroxyphenyl]-2-(1H)-quinolone.

6. 8-Methyl-6-[4-carbamoylphenyl]-2-(1H)-quinolone.

7. A pharmaceutical composition comprising a pharmaceutically acceptable carrier or diluent and an effective cardiac-stimulating amount of a compound as claimed in claim 1.

8. A method for stimulating cardiac activity in the treatment of a subject afflicted with congestive heart failure, which comprises administering to said subject an effective cardiac-stimulating amount of a compound as claimed in claim 1.

* * * * *